Figure 1:
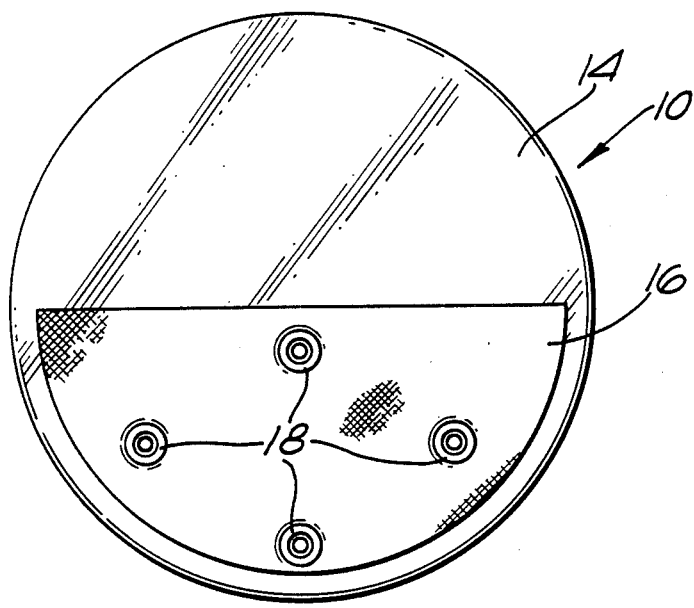

United States Patent [19]
Audretsch

[11] Patent Number: 4,950,292
[45] Date of Patent: Aug. 21, 1990

[54] TISSUE EXPANDERS

[75] Inventor: Werner Audretsch, Dusseldorf, Fed. Rep. of Germany

[73] Assignee: Dow Corning Corporation, Midland, Mich.

[21] Appl. No.: 340,958

[22] Filed: Apr. 20, 1989

[30] Foreign Application Priority Data

Apr. 20, 1988 [DE] Fed. Rep. of Germany ....... 8809294

[51] Int. Cl.$^5$ .......................... A61F 2/12; A61F 2/02
[52] U.S. Cl. ........................................ 623/8; 623/11
[58] Field of Search ........................ 623/7, 8, 11, 12

[56] References Cited
U.S. PATENT DOCUMENTS

| | | | |
|---|---|---|---|
| 4,264,990 | 5/1981 | Hamas | 623/8 |
| 4,426,742 | 1/1984 | Prahl | 623/7 |
| 4,615,704 | 10/1986 | Frisch | 623/8 |

FOREIGN PATENT DOCUMENTS

| | | | |
|---|---|---|---|
| 2742394 | 3/1979 | Fed. Rep. of Germany | 623/7 |
| 2607696 | 6/1988 | France | 623/8 |

Primary Examiner—David J. Isabella
Attorney, Agent, or Firm—Allan O. Maki; Howard W. Hermann

[57] ABSTRACT

A tissue expander capable of insertion in a human body to induce formation of a pocket into which a mammary prosthesis may be inserted including an expander portion which is flaccid and is adapted to be inflated progressively in the body to induce formation of said pocket, a support plate portion which is sufficiently flexible that it may be bent or folded upon itself for insertion into or removal from the body through an incision in the body and to recover to a plate-like condition within the body, feed tube and releasable fastener preferably a snap fastener whereby the support portion and the expander portion are connected together until it is desired to release the expander portion from the support portion.

9 Claims, 3 Drawing Sheets

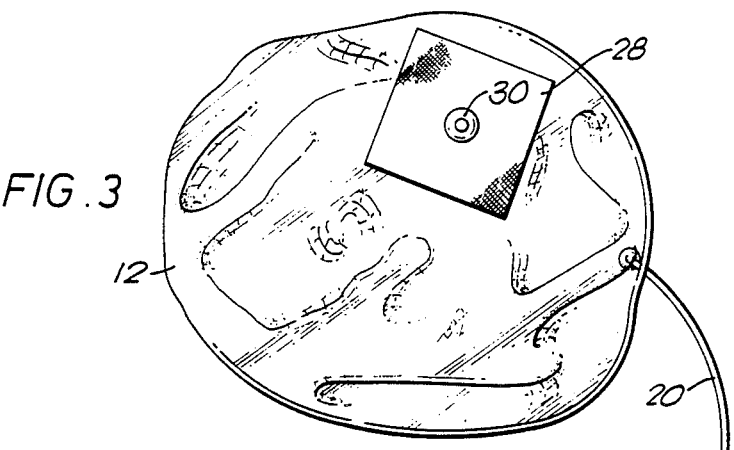
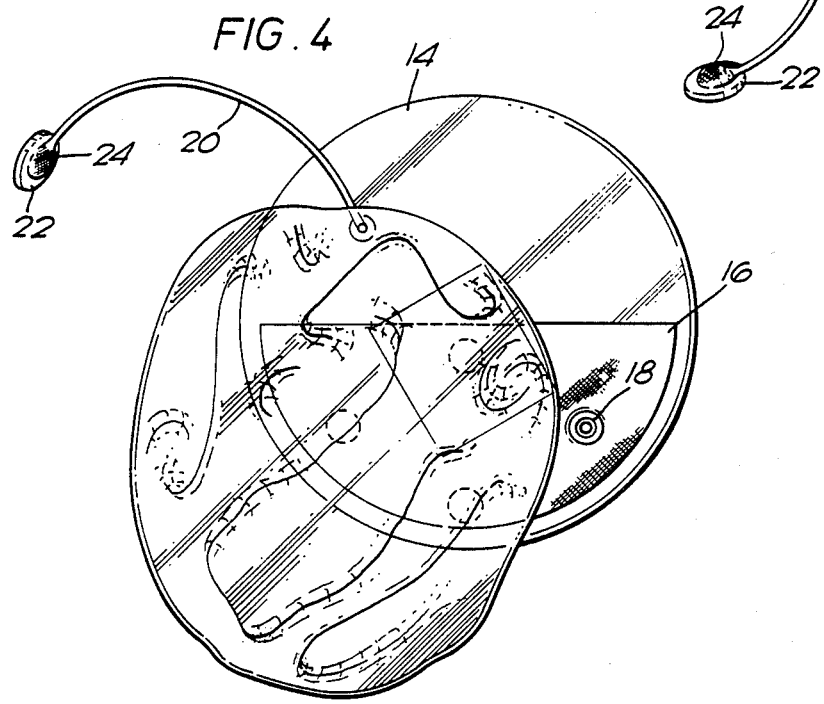

TISSUE EXPANDERS

This invention is concerned with tissue expanders and is particularly concerned with tissue expanders intended for use in surgical treatments of the human body to reconstruct the breast.

In the surgical treatment of the human body, it is a practice to insert prostheses to mimic the appearance and/or behaviour of parts of the body. For example in the case of mastectomy of the human breast it is a practice to provide the patient with a replacement breast in the form of a prosthesis. The prosthesis may be inserted in a pocket in the body, and it is a practice to induce formation of the desired pocket in the body by use of a tissue expander, to remove the expander from the pocket when it has been formed to the desired size and to insert the prosthesis into the pocket. Various designs of tissue expander are commercially available. Generally they comprise an inflatable envelope which is implanted in the body and progressively inflated over an extended time period of many weeks or months.

Insertion and correct location of the tissue expander in its collapsed state into the body can be a difficult operation due to the highly flexible nature of the expanders generally employed. Also, a difficulty arising from the use of simple expandable envelope tissue expanders is that as tissue develops during healing of the wound in which the expander has been placed, the tissue develops as a fibrous capsule and tends to develop in such a way that as the envelope is inflated to expand it, the fibrous capsule constrains the expansion of the expander so that it occurs in a somewhat spherical manner rather than the desired tear drop manner. This is especially the case if the tissue expander is inserted at the time of mastectomy and inflation of the expander to form the pocket is delayed, for example to minimise the risk of dehiscence. Such delaying of inflation is a practice, for example in those cases where the body tissue of the patient has become weakened, for example during pre-operative treatment.

In specification U.S. Pat. No. 4 264 990 there is disclosed a mammary prosthesis intended for insertion through a small incision into the body. The prosthesis disclosed therein comprises a soft front envelope portion of the inflatable or prefilled silicone elastomer type and a flexible backing of an inert polymeric material having internal passageways or compartments in which material is caused to rigidify and so stiffen the flexible backing. The stiffening is said to be beneficial in terms of the improved resistance to deformation of the prosthesis by body tissue developing around the prosthesis. Specification U.S. Pat. No. 4 264 990 is concerned with prostheses and is silent on the question of tissue expansion and particularly on the issue of the removal of an inflatable tissue expander from the body after a desired pocket has been formed by progressive inflation thereof and subsequent insertion of a selected prosthesis in the formed pocket.

There remains a need to provide a tissue expander which can be used, for example in reconstruction of the female breast immediately after subcutaneous or modified radical mastectomy, to give a pocket of desired shape for any particular patient.

The present invention provides in one of its aspects a tissue expander capable of insertion in a human body to induce formation of a pocket into which a mammary prosthesis may be inserted comprising (a) an expander portion which is flaccid and is adapted to be inflated progressively in the body to induce formation of said pocket, (b) a support plate portion which is sufficiently flexible that it may be bent or folded for insertion into or removal from the body through an incision in the body and to recover to a plate-like condition within the body, (c) feed tube means attached to the expander portion and having a valve through which inflating medium may be supplied into the expander portion, and (d) releasable securing means whereby the support portion and the expander portion are connected together until it is desired to release the expander portion from the support portion.

The present invention provides in another of its aspects in or for use in a tissue expander according to the invention a support plate portion of biocompatible silicone elastomer which is sufficiently flexible that it may be bent or folded for insertion into (or removal from) the body through an incision in the body to recover to a plate-like condition in the body, having secured thereto a portion of a releasable securing means adapted to cooperate with means secured to the expander portion to connect together the expander portion and the support portion until it is desired to release the expander portion from the support portion.

The present invention provides in another of its aspects in or for use in a tissue expander according to the invention an expander portion of biocompatible silicone material which is in the form of an envelope adapted to be inflated by introduction of saline solution thereto and which has secured thereto a portion of a releasable securing means adapted to cooperate with means secured to the support portion to connect together the expander portion and the support portion until it is desired to release the expander 30 portion from the support portion.

In a tissue expander according to the invention the expander portion (a) may comprise an envelope composed of any of those biocompatible materials (for example a silicone elastomer) employed in the commercially available inflatable tissue expanders. The envelope may be formed in known manner, for example by deposition of a silicone material on a mandrel followed by curing of the silicone to an elastomeric state. The envelope may be designed to develop a spherical, tear drop or other desired form when inflated.

In a tissue expander according to the invention the support plate portion (b) is sufficiently flexible that it may be bent or folded for insertion into, or removal from, the body through an incision in the body and to recover to a plate-like condition within the body. This feature is particularly important in respect of those tissue expanders which are intended to be introduced to the body through a comparatively small incision. The support portion serves to facilitate insertion and location of the expander portion (a), to support the expander portion in the body and to resist contraction of the fibrous capsule produced as scar tissue forms. It serves to form a substantially flat wall for the developing pocket and provides a pressure plate which serves to ensure that expansion of tissue induced by inflation of the expander portion (a) takes place in a direction outwardly of the body. It thus serves to protect the expander portion somewhat from unwanted stresses which might otherwise be caused by developing tissue as the incision heals and as the expander portion is progressively inflated. The support portion (b) is in the form of a plate which preferably has a maximum width greater than the maximum diameter of the expander portion (a) and which preferably is thicker at its mid-regions than at its outer regions and may thus be, for example, concavo-convex or plano-convex when viewed in section. The support portion may have any appropriate shape, for example pear shaped or circular. Preferably the support portion is a moulding of a biocompatible silicone elastomer. Preferably the support portion has a hardness of about 60 durometer. Suitably, the expander portion (a) prior to inflation has a maximum diameter of about 70% to 90% of the maximum diameter or width of the support portion or a significant portion thereof. For example a support portion (b) for use with a tissue expander portion (a) having a capacity of 400 to 600 cc may comprise a domed, circular or pear shaped plate of biocompatible material having a circular portion the diameter of which is of the order of about 130 to 140 mm. Preferably the expander portion (a) is located on the support portion (b) so that the periphery of the expander portion at that edge which is to be lowermost in the patient's body is in register with the periphery of the support portion. In this way the pocket induced by the tissue expander may be caused to have appropriate ptosis.

In a tissue expander according to the present invention the expander portion is mounted on the support portion and is releasably secured thereto by the releasable securing means. This means is preferably such that the portions can be connected with each other so that the expander portion (a) may be rotated through 360 degrees relative to the support portion (b) even though the portions (a) and (b) are secured together. In this way the surgeon inserting the tissue expander may locate the support portion as desired in the body with the expander portion secured thereto through the releasable securing means and then rotate the expander portion (a) on the support portion (b) so that the valve of the feed tube of the means (c) is located as desired by the surgeon. The releasable securing means is such that the portions are detachable one from the other, so that after the expander portion is no longer required in the body it can be detached from the support portion and removed from the body without removing the support portion from the body if desired. The fastening means may comprise one or more fastener elements on one of said portions and a cooperating fastener element or elements on the other of said portions located so that one or more cooperating fastener elements may be engaged. It is possible to employ a button and buttonhole type arrangement, but in a most preferred form of the invention, the means comprises mechanical fastener means comprising one or more snap fastener means. Suitable snap fastener means include those of metal or biocompatible materials (e.g. medically acceptable grades of stainless steel, titanium, polysulphones or polycarbonate) which are of known design in which a first portion comprises a spigot or male element which is adapted to engage and to be resiliently retained within a second or female portion. Preferably the female portion of the snap fastener means is mounted in the support portion so that the surface of the support portion bears no significantly obtrusive features which might impede sliding of a mammary implant prosthesis located contiguous thereto, as may occur for example when the support portion is not removed from the patient when the expander portion is removed. The use of a single fastener element located, for example centrally of the surface of the expander portion, is desirable in order to enable inflation of the expander portion in a uniform way without significant distortion of the expander portion, which might occur, for example if several fastener elements were secured thereto. A single snap fastener element may be employed on the support portion and is preferably located lower than the centre thereof so that the centre of the expander portion may be located lower on the patient's body than the centre of the support portion, whereby to promote desired ptosis. It is also possible to provide the support portion with several snap fastener elements disposed so that any one of them may be caused to co-operate with the snap fastener element on the expander portion so that the mutual disposition of the support portion and expander portion can be adjusted readily prior to or during introduction to the body. In this way the disposition of the expander portion upon the support portion may be selectively varied in accordance with the characteristics of the incision in which the tissue expander is to be inserted, the desired location of the remote valve and the disposition of the pocket desired to be induced. In embodiments hereinafter described, a portion of at least one snap fastener is affixed to one of the said portions (a) and (b) and a cooperating portion of at least one snap fastener is affixed to the other of the said portions. The preferred snap fastener means permits a sufficiently secure fixing together of the said portions without significantly adversely affecting the ability of the expander portion to maintain a desired shape during inflation, and also provides the possibility to disengage the elements of the snap fastener when desired. The snap fastener elements may be mounted in reinforcing elements in the form of sheets or strips of, for example fabric, plastic, or fabric reinforced rubber which may be secured to or in the respective portions as by stitching, moulding, adhesive or other suitable means.

A tissue expander according to the invention may be used, for example in reconstruction of the female breast immediately or delayed after subcutaneous or modified radical mastectomy. The support portion may be inserted, for example in a sub pectoral pocket in the body with the expander portion attached to it in the desired position by the securing means. It has been found that the introduction of the device into the body and proper location of the expanding portion can be facilitated by wrapping or rolling the support plate (b) around the expander portion (a). As aforesaid, the expander portion is so located that the remote valve is satisfactorily located, and that the pocket induced will be of appropriate shape and size to receive a mammary prosthesis with appropriate location, orientation and ptosis. It is possible to delay inflation of the expander portion, e.g. with saline solution, until risk of dehiscence is reduced, the support portion serving to control development of the fibrous capsule. The expander portion may then be inflated to the desired extent progressively over a period of several weeks or months. After a period of about six months, the expander portion, and if desired the support portion, may be removed from the patient and replaced by a mammary prosthesis of known type, for example one composed of suitable silicone materials such as a shaped flexible sac filled with silicone gel. The support portion, when allowed to remain in the patient serves to support the prosthesis and this may be beneficial in some cases.

By use of a tissue expander according to the invention one may achieve one or more advantages, for example, one may commence reconstruction of the breast and provide at least a semblance of a breast immediately after mastectomy without significant risk of dehiscence to overlying flaps of tissue; insertion of the expander portion is facilitated by stability conferred by the support portion, stability of location is conferred on the expander portion and some protection for the ribs is afforded by the support portion during inflation of the expander portion; one may induce a pocket of desired shape for any particular patient and so permit improved disposition and ptosis of the subsequently inserted prosthesis. In the event of deflation of the expander portion, the support portion serves to maintain the integrity of the already formed fibrous capsule. Also, in the event that it becomes necessary to drain a seroma, when using the preferred tissue expander, the disposition of the support portion and the expander portion ensures that a portion of the developing pocket above the expander portion in the patient may be entered with a hypodermic needle with minimal risk of puncturing the expander portion.

There now follows a detailed description to be read in conjunction with the accompanying drawings of two examples of tissue expander provided by the invention and illustrative thereof. In the drawings.

Figure 2:
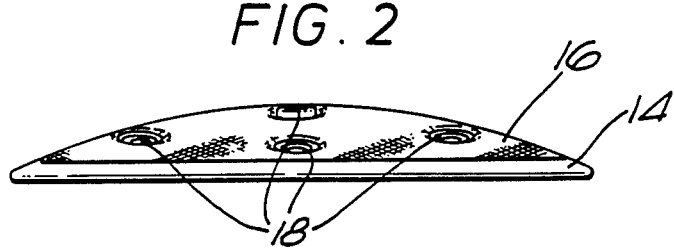
Figure 5:
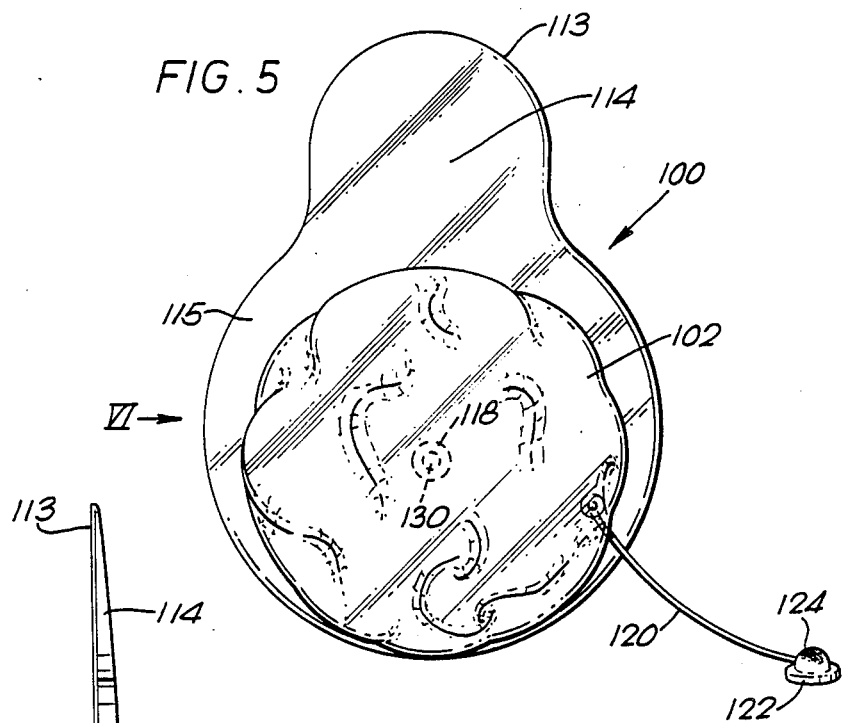
Figure 6:
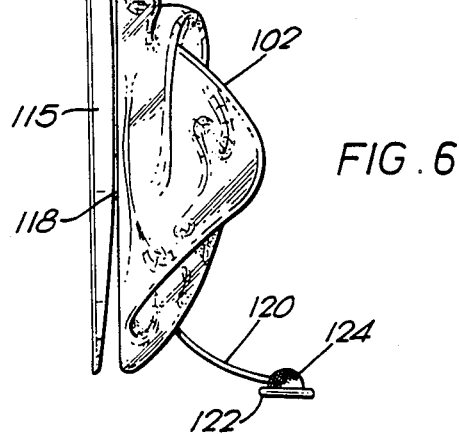

FIG. 1 is a plan view of a support element (10) of the first illustrative tissue expander, FIG. 2 is a side elevation of the support element (10), FIG. 3 is a view of an expander portion (12) of the first illustrative tissue expander in unexpanded condition, FIG. 4 is a view of the first illustrative tissue expander with the support portion (10) and expander portion (12) assembled ready for use, FIG. 5 is a plan view of the second illustrative tissue expander, and FIG. 6 is a side elevation of the second illustrative tissue expander.

The first illustrative tissue expander comprises a support portion (10) (FIGS. 1, 2 and 4) and an expander portion (12) (FIGS. 3 and 4). The support portion (10) is formed of a biocompatible material, for example a silicone rubber and is in the form of a shallow domed circular plate (14). The plate (14) is thicker in its mid region than at its outer regions and the plate is comparatively stiff in its mid region and flexible in its outer regions. A fabric reinforced silicone rubber sheet (16) is secured to the convex surface of the plate, covering a part of the plate as shown in FIGS. 1 and 2. Four female snap fastener elements (18) are mounted in the sheet (16) and are arranged symmetrically with respect to each other but are all disposed to that side of a diameter of the plate (10) which is intended to be lowest in the patient's body.

The expander portion (12) (shown in FIG. 3) comprises an envelope of biocompatible silicone elastomer which is designed to cooperate with the support portion (10) to produce a generally tear drop shaped pocket when expanded. A silicone rubber tube (20) is connected to the envelope and to an injection button (22) of conventional design having a self sealing button dome (24) of, for example biocompatible silicone elastomer, mounted on a rigid base to permit inflation of the envelope by injection of fluid for example saline solution. A fabric reinforced silicone rubber sheet (28) is secured to the rear surface of the envelope. A male snap fastener element (30) is secured to the sheet (28), the construction and arrangement being such that the element (30) is positioned offset from the centre region of the rear surface of the envelope.

The plate and expander portions are assembled together (FIG. 4) with the male snap fastener element (30) in co-operating engagement with a chosen one of the female snap fastener elements (18). In this way the relative disposition of the envelope to the plate may be varied to suit the shape and configuration of the incision in the body to be treated and the location of the pocket in the expanded tissue induced by expansion of the expander portion (12). In addition, the expander portion may be rotated on its snap fastener connection (30, 18) upon the support portion (10) to position the button (24).

The second illustrative tissue expander comprises a support portion (100) and an expander portion (102) (FIG. 5). The support portion (100) comprises a plate (114) of a biocompatible silicone rubber. The plate (114) is generally pear shaped and is intended to be placed in the body with its narrower portion (113) disposed higher in the patient's body than its wider portion (115). The plate (114) is thicker in its mid regions than at its outer regions with the mid regions of the wider portion (115) being thickest. The plate is comparatively stiff in its mid regions and flexible in its outer regions. A female snap fastener element (118) is mounted in a Dacron reinforcement and moulded in the plate with its outer surface flush with the convex surface of the plate 114. The element (118) is located a little below the mid point of the wider portion (115).

The expander portion (112) comprises an envelope of biocompatible silicone elastomer which is designed to have a generally tear drop shape when expanded. Its diameter prior to inflation is less than that of the wider portion (115) of the plate (114). A silicone rubber tube (120) is connected to the envelope and to an injection button (122) of conventional design having a self sealing button dome (124) of, for example, biocompatible silicone elastomer, mounted on a rigid base to permit inflation of the envelope by injection of fluid for example saline solution. A fabric reinforced silicone rubber sheet (128) (not shown) is vulcanised to the rear surface of the envelope. A male snap fastener element (130) is secured to the sheet (128), the construction and arrangement being such that the element (130) is positioned centrally of the envelope.

The plate and expander portions are assembled together (FIG. 5) with the male snap fastener element (130) in co-operating engagement with the female snap fastener element (118). The expander portion may be rotated on its snap fastener connection (130,118) upon the support portion (110) to position the button (124). The plate and expander together can be used to generate a tear drop shaped pocket which is particularly satisfactory considered from the viewpoint of side and front elevations.

The illustrative tissue expanders may be used in a variety of surgical techniques, and in particular, the initial inflation of the expander portion may be initiated at the time of insertion of the tissue expander in the body or subsequently. In one mode of use, the illustrative tissue expanders may be located as desired in an incision in the body, which may be for example made at the time of mastectomy. The plate portion (10 or 110) is located on the patient with the expander portion (12,112) exposed on the plate portion. The incision is then surgically closed over the inserted tissue expander with the button dome (24,124) located in a position convenient for access with a hypodermic needle. Inflation of the envelope is commenced when the risk of dehiscence is sufficiently reduced and the envelope is then progressively expanded over a period of time until the desired shaping has occurred, Thereafter, the expander portion (12,112) is surgically removed and replaced with a suitable mammary prosthesis. The support portion (10,110) is generally removed with the expander portion (12,112), but in certain cases it may be beneficial to release the snap fastening (30,18 or 130,118) in order to detach the expander portion from the support portion, so that the support portion can be allowed to remain in place.

That which is claimed is:

1. An implantable tissue expander system for insertion in a human body to induce formation of a pocket into which a mammary prosthesis may be inserted comprising (a) an inflatable member which is flaccid and is adapted to be inflated progressively in the body to induce formation of said pocket, (b) a separate support plate which is sufficiently flexible that it may be bent or folded for insertion into or removal from the body through an incision in the body and to recover to its original condition within condition within the body, (c) feed tube means attached to the inflatable member and having a valve through which inflating medium may be supplied into the inflatable member and (d) cooperating releasable securing means on each of the inflatable member and the support plate whereby the support plate and the inflatable member are connected together until it is desired to release the inflatable member from the support plate.

2. A tissue expander according to claim 1 wherein the releasable securing means comprises at least one snap fastener.

3. A tissue expander according to claim 2 wherein a male portion of the snap fatener is secured to the inflatable member and a female portion of said snap fastener is secured to the support plate.

4. A tissue expander according to claim 2 comprising a plurality of fastener elements on either one of said inflatable member or support plate and a co-operating fastener element on the other of said inflatable member or support plate may be engaged with any one of the plurality of fastener elements.

5. A tissue expander according to claim 1 wherein the support plate has a generally circular shape and is thicker at its midregion than at its outer regions.

6. A tissue expander according to claim 1 wherein the inflatable expander portion comprises an envelope which may be inflated to a spherical form having a diameter approximately 70% to 90% of the maximum width of the support portion.

7. A tissue expander according to claim 1 wherein the securing means comprises a first portion located centrally on a surface of the inflatable member adjacent to the support plate, and a second portion located on a surface of the support plate adjacent the expander portion, which second portion is adapted to co-operate with the first portion and is located offset from the center of the support plate.

8. A tissue expander according to claim 1 wherein the support plate comprises a biocompatible silicone elastomer.

9. A tissue expander according to claim 1 wherein the inflatable member comprises a biocompatible silicone elastomer.

* * * * *